United States Patent

Lee et al.

[11] Patent Number: 6,111,637
[45] Date of Patent: Aug. 29, 2000

[54] APPARATUS AND METHOD FOR EXAMINING WAFERS

[75] Inventors: Young-Ho Lee; Sang-Kyu Hahm; Young-Kyu Lim; Byoung-Seol Ahn, all of Suwon, Rep. of Korea

[73] Assignee: Samsung Electronics Co., Ltd., Suwon, Rep. of Korea

[21] Appl. No.: 08/768,710

[22] Filed: Dec. 18, 1996

[30] Foreign Application Priority Data

Dec. 29, 1995 [KR] Rep. of Korea .................. 95-65737

[51] Int. Cl.[7] ............................ G01N 21/00; H04N 7/18; B65G 49/07
[52] U.S. Cl. ................. 356/237.1; 382/149; 348/126; 250/559.41; 414/331.18; 414/331; 414/757; 414/935; 414/936; 414/937; 414/940; 324/158.1
[58] Field of Search ................ 356/237.1; 382/148, 382/149; 348/126; 250/559.41; 414/331.18, 331, 757, 935, 936, 937, 940; 324/158.1

[56] References Cited

U.S. PATENT DOCUMENTS

| | | | |
|---|---|---|---|
| 4,644,172 | 2/1987 | Sandland et al. | 250/548 |
| 4,818,169 | 4/1989 | Schram et al. | 414/331 |
| 4,938,654 | 7/1990 | Schram | 414/757 |
| 5,105,147 | 4/1992 | Karasikov et al. | 324/158 E |
| 5,488,292 | 1/1996 | Tsuta | 324/158.1 |

*Primary Examiner*—Jeffrie R. Lund
*Attorney, Agent, or Firm*—Jones Volentine, LLP

[57] ABSTRACT

A method and an apparatus for examining wafers includes a wafer cassette having a capacity for holding a plurality of wafers located on each of first and second locaters. The wafer cassettes are fixedly held on the first and second locaters during the wafer examination. A first indicator shows that the wafer cassettes are fixedly held on the first and second locaters. A robot arm sequentially carries each of the wafers between the first locator, an aligner, a scanning chamber and the second locater to examine the wafers. The wafer cassettes are released when the examination is complete, and a second indicator shows that the examination is complete.

12 Claims, 4 Drawing Sheets

APPARATUS AND METHOD FOR EXAMINING WAFERS

BACKGROUND OF THE INVENTION

1. Field of the Invention

The present invention relates to an apparatus and method for examining wafers, and more particularly, to an apparatus and method for examining wafers, by which the operator can easily perceive the completion of the wafer examining process steps. The wafers are held until their examination is completed, whereby the wafers are prevented from being broken due to carelessness of the operator while the operator works by the system.

2. Description of the Related Art

FIG. 1 shows a conventional apparatus for examining wafers. Referring to FIG. 1, first and second locators 9A and 9B, and an aligner 6 are disposed around a scanning chamber 7. Wafer cassettes 10 are loaded one-by-one on the first and second locators 9A and 9B. The aligner 6 aligns the flat zone of the wafer 5 picked up from the wafer cassette 10 by a robot arm 4.

In the meantime, a system controller 2, electrically connected to the scanning chamber 7, displays the resultant data of an examined wafer on a monitor 8. When a start switch 1 is operated, the system controller 2 operates the robot arm 4 according to a preset program by means of a robot controller 3.

Following is a brief description of a process for examining the wafers in the wafer cassette 10 by the conventional apparatus. When an operator turns on the start switch 1 after loading a wafer cassette 10 on the first locator 9A, the system controller 2 outputs an operational control signal to the robot controller 3, so that the robot arm 4 picks up one of the wafers in the wafer cassette 10 and then carries the picked-up wafer to the aligner 6. The aligner 6 aligns the flat zone of the carried wafer. The wafer is moved to the scanning chamber 7 where the wafer is scanned to determine whether or not particles remain on the wafer. The resultant data of the scanned wafer are inputted into the system controller 2 and then displayed on the monitor 8 by the system controller 2.

After the resultant data are displayed on the monitor 8, the robot arm 4 carries the scanned wafer to the wafer cassette 10 loaded on the second locator 9B.

In the conventional apparatus for examining wafers, since the wafer is moved to the wafer cassette 10 loaded on the second locator 9B after the resultant data are displayed on the monitor 8, the operator can erroneously pick up the wafer cassette 10 from the second locator 9B in order to carry the wafer cassette 10 to another area before all of the wafers in the wafer cassette 10 are examined. More specifically, when the operator picks up the wafer cassette 10 from the second locator 9B, after he confirms the resultant data of the last wafer displayed on the monitor 8 but before the last wafer from the first locater 9A is completely carried to the wafer cassette 10 on the second locator 9B, the last carried wafer may collide with the wafer cassette 10 or other structures. Such collisions may break the wafer, thereby degrading the yield of the semiconductor devices.

SUMMARY OF THE INVENTION

Accordingly, it is an object of the present invention to overcome the one or more of the above-described problems of the conventional art by providing an apparatus and a method for examining wafers, by which the operator can easily perceive the completion of the wafer examining process steps. The wafers are held until their examination is completed, whereby the wafers are prevented from being broken due to carelessness of the operator while the operator works by the system.

To achieve these and other objects, the present invention provides an apparatus for examining wafers in a scanning chamber of the apparatus, the apparatus comprising: a system controller including a start switch and a display, the system controller displaying data outputted from the scanning chamber on the display when the start switch is operated, the system controller generating a first control signal and a second control signal; a wafer cassette having a capacity for holding a plurality of wafers located on each of first and second locaters; means for fixedly holding the wafer cassette for a designated time period in response to the first control signal; a first means for indicating that the wafer cassettes are fixedly held on the first and second locaters; an aligner for aligning a flat zone of the wafers; and means for controlling operation of a robot arm according to the second control signal, the robot arm sequentially carrying the wafers between the first locator, the aligner, the scanning chamber and the second locater to examine the wafers.

BRIEF DESCRIPTION OF THE DRAWINGS

The above objects, and other features and advantages of the present invention will become more apparent by describing in detail preferred embodiments thereof with reference to the attached drawings, in which.

DETAILED DESCRIPTION OF PREFERRED EMBODIMENTS

Figure 1:
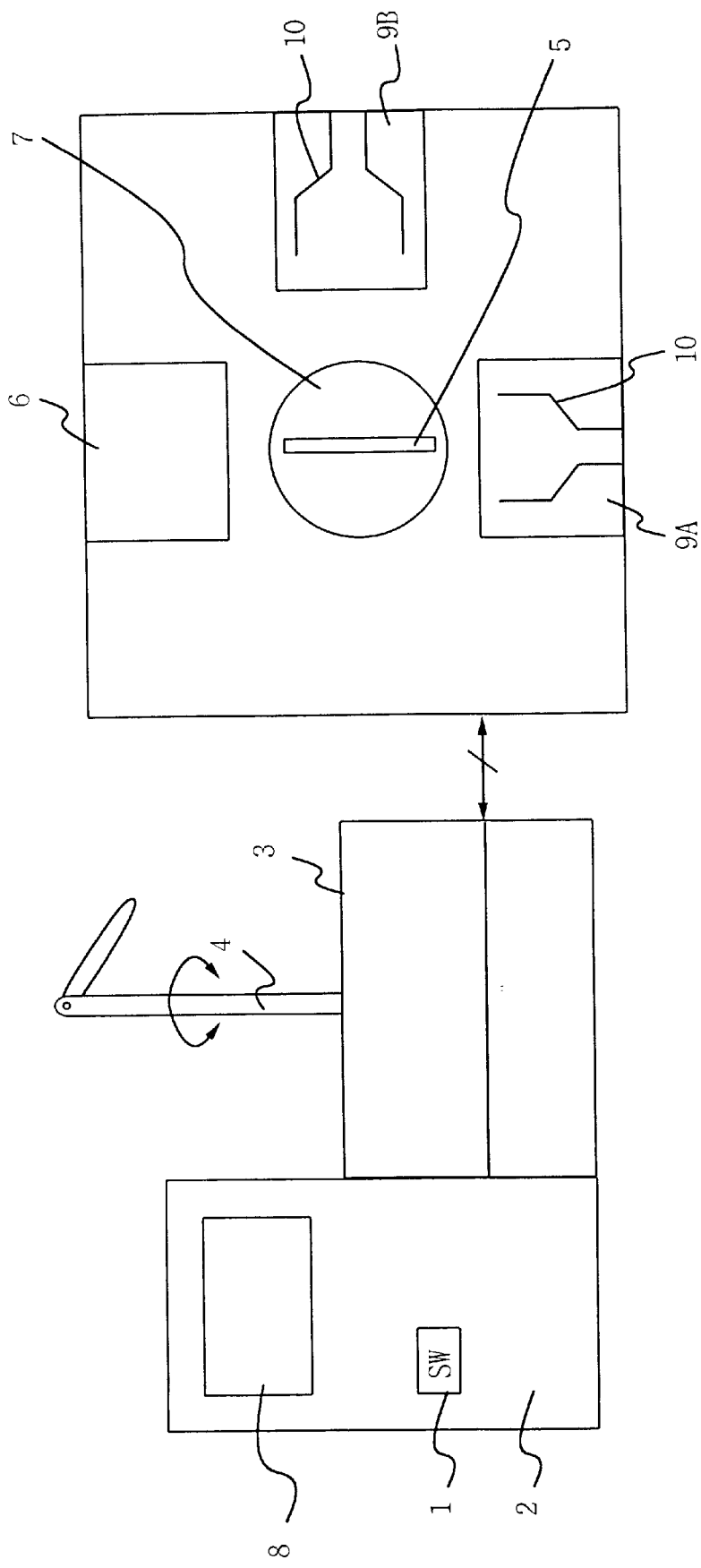
FIG. 1 is a schematic view of a conventional apparatus for examining wafers.

A preferred embodiment of the present invention will be described in detail with reference to the accompanying drawings, with like reference numerals referring to the same or like elements in the following description.

Figure 2:
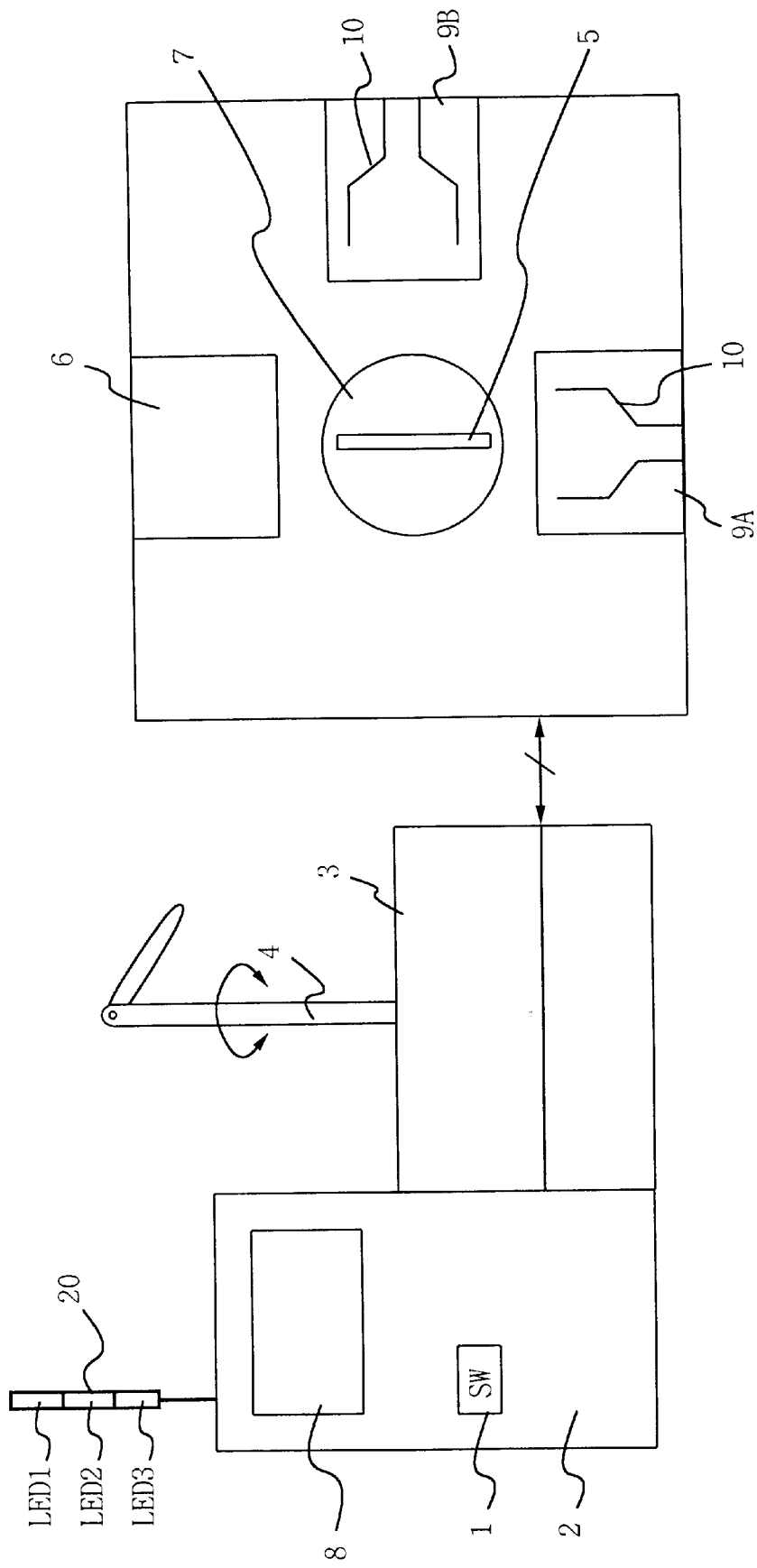
FIG. 2 is a schematic view of an apparatus for examining wafers according to the present invention.
Figure 3:
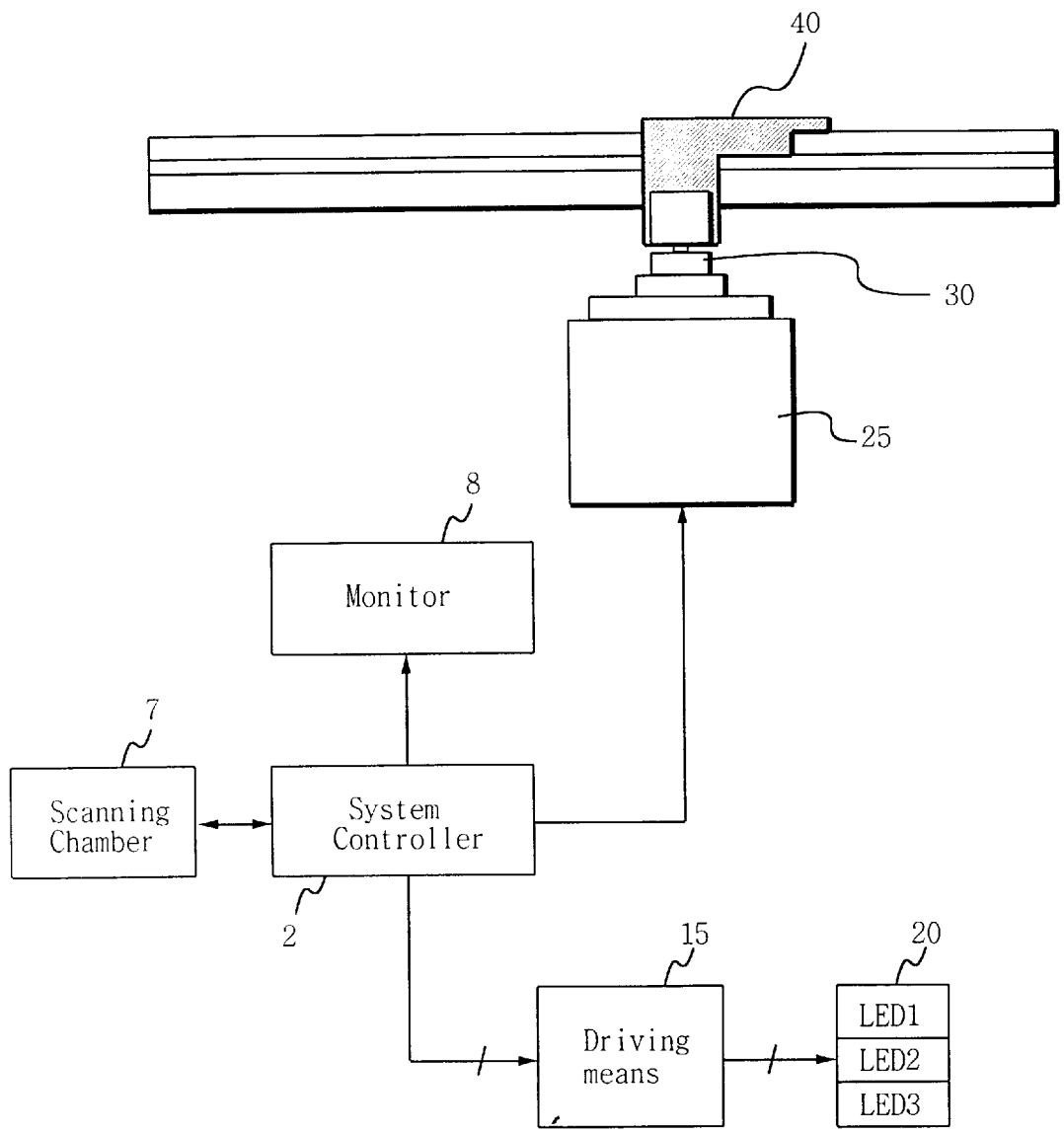
FIG. 3 is a block diagram of the apparatus shown in FIG. 2, which shows the detailed construction of a holder installed in a locator.

FIG. 2 is a schematic view of an apparatus for examining wafers according to the present invention, and FIG. 3 is a block diagram of the apparatus shown in FIG. 2, in which the construction of a holder installed in a locator is depicted in detail.

Referring to FIGS. 2 and 3, the apparatus of the present invention includes a system controller 2 for controlling the operation of surrounding systems. When a start switch installed at a body of the apparatus is turned on, the system controller 2 receives data supplied from a scanning chamber 7 and displays the data on a monitor 8. A robot controller 3 operates a robot arm 4 so as to carry wafers 5 in a wafer cassette 10 along a predetermined path according to a control signal from the system controller 2.

First and second locators 9A and 9B respectively include a holder 40 (FIG. 3) for holding the wafer cassette 10. The holder 40 is pivotally connected to a transmission shaft 30 of a holder driving means 25. The holder driving means 25 is operated by a predetermined driving signal outputted from the system controller 2.

An indicator 20 includes first, second, and third light-emitting diodes LED1, LED2, and LED3. The indicator indicates the steps that the wafers 5 are loaded by the robot arm 4, and that the holder driving means 25 is operating according to the data from the system controller 2.

Figure 4:
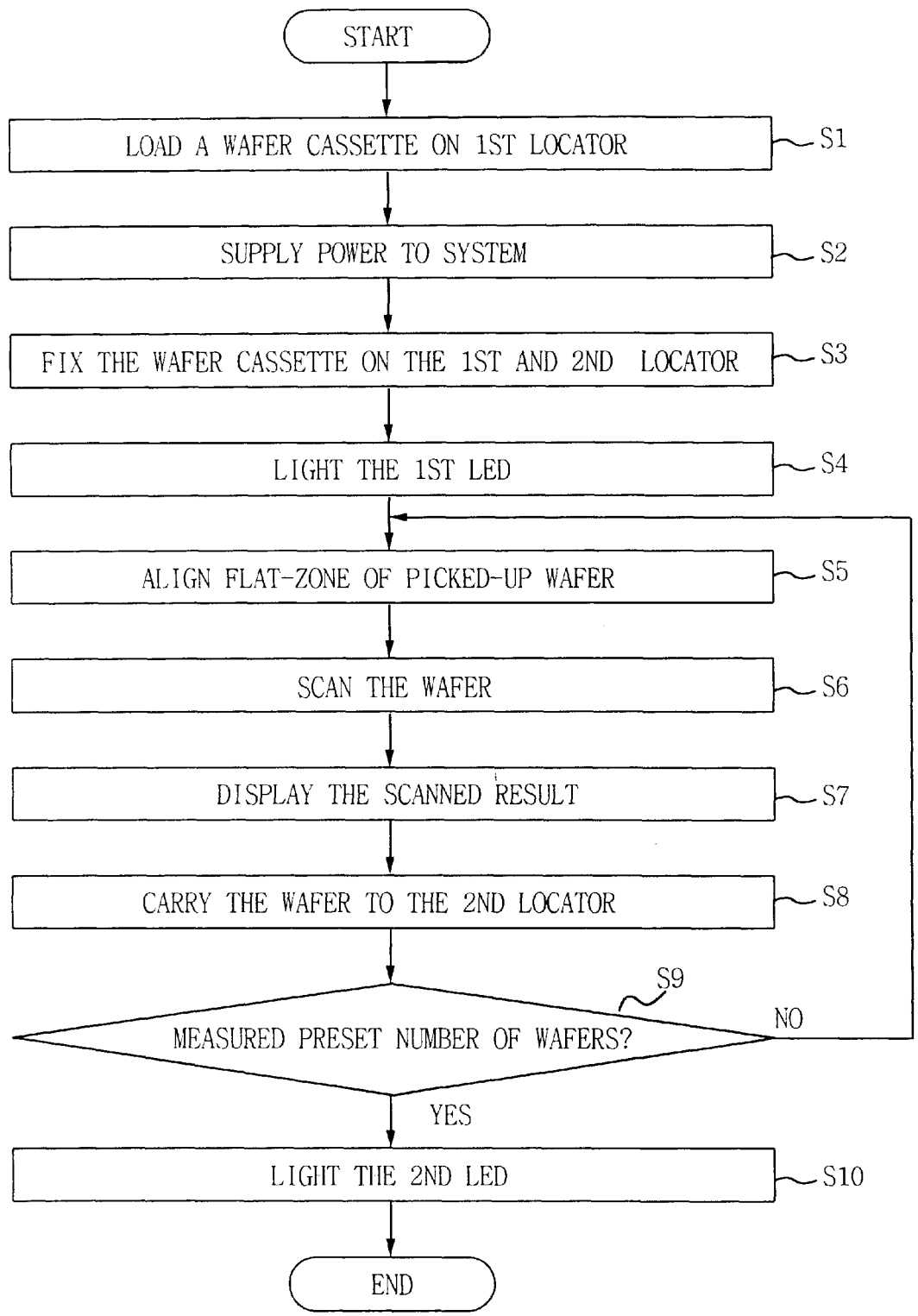
FIG. 4 is a flow chart of a method for examining wafers according to the present invention.

Hereinafter, a method for examining wafers by the apparatus having the above-described construction according to the present invention will be discussed in detail with reference to the flow chart shown in FIG. 4.

First, a wafer cassette 10 containing a plurality of wafers 5 is loaded on the first locator 9A (step S1). An empty wafer cassette 10 is loaded on the second locater 9B. Thereafter, the operator turns on the start switch 1 installed at the body of the system (step S2).

When the start switch 1 is turned on, the system controller 2 outputs a driving control signal for a predetermined time so that the holder 40 holds the cassette 10. The holder driving means 25 shown in FIG. 3, which is operated by the driving control signal, rotates the transmission shaft 30, and thereby the holders 40 fix the cassettes 10 loaded on the first and the second locators 9A and 9B (step S3).

When the cassette 10 is fixed by the holder 40, the system controller 2 supplies data to a driving means 15 so as to light up the first light-emitting diode LED1. When the first light-emitting diode LED1 is lit, the operator can readily and optically perceive the state that the cassette 10 is held (step S4).

When the cassette 10 is held by the holder 40 and the first light-emitting diode LED1 is lit, the system controller 2 operates the robot controller 3. In this case, the robot arm 4 picks up one of the wafers 5 in the cassette 10 on the first locater 9A and carries the selected wafer 5 to the aligner 6. Then, the aligner 6 aligns the flat zone of the wafer 5 (step S5).

The aligned wafer 5 is then moved into the scanning chamber 7 by the robot arm 4. Thereafter, the wafer 5 is examined in the scanning chamber 7 to determine if particles remain thereon, and the resultant data of the examination is supplied to the system controller 2 (step S6).

The system controller 2 displays the resultant data on the monitor 8 (step S7). Thereafter, the wafer 5 examined in the scanning chamber 7 is carried to, and placed into, the cassette 10 loaded on the second locator 9B (step S8).

When the wafer 5 is housed in the cassette 10 loaded on the second locator 9B, the system controller 2 determines if all of the wafers in the wafer cassette on the first locator 9A, or a preset number of the wafers, have been examined (step S9). In case where all of the wafers have not been examined yet, steps S5–S9 are repeated.

In the meantime, when all of the wafers have been examined, the system controller 2 lights the second light-emitting diode LED2 for a predetermined time (step S10). The luminescence of the second light-emitting diode LED2 enables the operator to optically perceive that the examination of the wafers in the wafer cassette on the first locator 9A has been completed.

After the second light-emitting diode LED2 is lit in step S10, the operator can turn off a stop switch (not shown), so that the holder 40 releases the wafer cassette 10 and moves to its initial position, and thereby the wafer cassette 10 can be separated from the second locator 9B.

If the system malfunctions in the course of the above described examination, the system controller 2 may preferably light the third light-emitting diode LED3, allowing the operator to take the proper action.

According to the present invention as described above, the wafer examining process steps are indicated by an indicator including a plurality of LEDs. As such, the wafers are prevented from colliding with the wafer cassette, and the wafer cassette can be carried safely. Further, the operator can safely and effectively work a plurality of examining systems simultaneously.

While the present invention has been particularly shown and described with reference to the particular embodiment thereof, it will be understood by those skilled in the art that various changes in form and details may be effected therein without departing from the spirit and scope of the invention as defined by the appended claims.

What is claimed is:

1. An apparatus for examining wafers, said apparatus comprising:

a scanning chamber in which the wafers are examined;

a system controller including a start switch and a display, said system controller being operatively connected to said scanning chamber so as to display data outputted from said scanning chamber on said display when said start switch is operated;

a wafer supplying cassette and a wafer receiving cassette each having a capacity for holding a plurality of wafers;

first and second locators adjacent said scanning chamber, said wafer supplying cassette being mounted to said first locator, and said second locator including a second locator holder operable to fix said wafer receiving cassette thereto and release said wafer receiving cassette;

second locator holder driving means, responsive to said system controller and operatively connected to said second locator holder, for selectively operating said holder to fixedly hold and release said wafer receiving cassette;

an aligner for placing a wafer in an aligned reference position in preparation for examination of the wafer in said scanning chamber;

a robot arm having a working range encompassing said locators, said aligner and said scanning chamber;

a robot controller, responsive to said system controller, for controlling said robot arm to carry wafers sequentially from the wafer supplying cassette mounted at said first locator, to said aligner, to said scanning chamber and to the wafer receiving cassette held at said second locator; and indicating means, responsive to said system controller, for indicating that all of the wafers provided in said wafer supplying cassette have been examined in said scanning chamber.

2. An apparatus as claimed in claim 1, and further comprising switching means for causing said second locator holder driving means to operate the holder to release said wafer receiving cassette.

3. An apparatus as claimed in claim 2, wherein said indicating means is also for indicating that said wafer receiving cassette is fixedly held at said second locator by said second locator holder.

4. An apparatus as claimed in claim 3, wherein said indicating means is also for indicating that said apparatus for examining wafers is malfunctioning.

5. An apparatus as claimed in claim 4, wherein said indicating means comprises a first light-emitting diode dedicated to indicate whether said wafer receiving cassette is fixedly held at said second locator, a second light-emitting diode dedicated to indicate whether the wafers have all been examined in said scanning chamber, and a third light-emitting diode dedicated to indicate a malfunction in the operation of the apparatus.

6. An apparatus as claimed in claim 1, wherein said first locator includes a first locator holder operable to fix said wafer supplying cassette thereto and to release said wafer supplying cassette, and further comprising a first locator holder driving means, responsive to said system controller and operatively connected to said first locator holder, for selectively operating said first locator holder to fixedly hold and release said wafer supplying cassette.

7. An apparatus as claimed in claim 6, wherein said first locator holder is a clamp, and said first locator holder driving means comprises a rotary driven transmission shaft coupled to the clamp.

8. An apparatus as claimed in claim 1, wherein said second locator holder is a clamp, and said second locator holder driving means comprises a rotary driven transmission shaft coupled to the clamp.

9. A method for examining wafers using a wafer examining apparatus, said method comprising the steps of:
   (1) loading a first wafer cassette on a first locator and a second wafer cassette on a second locator, said first wafer cassette containing a first number of wafers;
   (2) fixing said second wafer cassette in place at said second locator;
   (3) picking a wafer from said first wafer cassette loaded on said first locator;
   (4) placing the wafer that was picked up from said first wafer cassette in an aligned position in preparation for its examination;
   (5) transferring the aligned wafer into a scanning chamber, and scanning said wafer in the scanning chamber to obtain scanning data;
   (6) displaying the scanning data on a monitor;
   (7) carrying said wafer from said scanning chamber to, and placing said wafer into, said second wafer cassette while said second wafer cassette remains fixed in place at said second locator;
   (8) determining if the number of wafers carried to and placed into said second wafer cassette is equal to said first number of wafers provided in said first wafer cassette when the first wafer cassette was loaded onto the first locator;
   (9) repeating said steps 3–8 until the number of wafers in said second cassette is equal to said first number;
   (10) lighting a light-emitting diode once said number of wafers in said second cassette is equal to said first number; and
   (11) releasing said second wafer cassette from said second locator once said light-emitting diode has been lit.

10. The method of claim 9, and further comprising the steps of:
   fixing said first wafer cassette in place at said first locator before the wafers are picked therefrom; and
   releasing said first wafer cassette from said first locator once the number of wafers in said second cassette is equal to said first number.

11. The method of claim 10, and further comprising the step of:
   lighting another light-emitting diode when said apparatus for examining wafers is malfunctioning.

12. The method of claim 10, and further comprising the step of:
   lighting another light-emitting diode when both of said first and second wafer cassettes are fixed at said first and second locators, respectively.

* * * * *